United States Patent [19]

Paradis

[11] Patent Number: 5,334,142
[45] Date of Patent: Aug. 2, 1994

[54] SELECTIVE AORTIC PERFUSION SYSTEM

[75] Inventor: Norman A. Paradis, Brooklyn, N.Y.

[73] Assignee: New York University, New York, N.Y.

[21] Appl. No.: 756,693

[22] Filed: Sep. 9, 1991

[51] Int. Cl.$^5$ .......................................... A61M 31/00
[52] U.S. Cl. .................................. 604/53; 600/18; 604/96; 606/194; 206/364
[58] Field of Search .................. 600/18; 606/194; 604/23, 28, 49, 53, 96, 97; 206/363-364, 438; 261/DIG. 28

[56] References Cited

U.S. PATENT DOCUMENTS

| | | | |
|---|---|---|---|
| 4,448,188 | 5/1984 | Loeb | 128/6 |
| 4,459,977 | 7/1984 | Pizon et al. | |
| 4,473,067 | 9/1984 | Schiff | |
| 4,493,697 | 1/1985 | Krause et al. | |
| 4,522,302 | 6/1985 | Paikoff | 206/570 |
| 4,527,549 | 7/1985 | Gabbay | |
| 4,531,936 | 7/1985 | Gordon | 604/49 |
| 4,569,332 | 2/1986 | Schiff et al. | |
| 4,601,706 | 7/1986 | Aillon | |
| 4,644,936 | 2/1987 | Schiff | |
| 4,646,719 | 3/1987 | Neuman et al. | |
| 4,697,574 | 11/1987 | Karcher et al. | |
| 4,733,652 | 3/1988 | Kantrowitz et al. | |
| 4,741,328 | 5/1988 | Gabbay | |
| 4,804,358 | 2/1989 | Karcher et al. | 600/17 |
| 4,850,969 | 7/1989 | Jackson | |
| 4,927,623 | 5/1990 | Long, Jr. | |
| 4,943,277 | 7/1990 | Bolling | 604/96 |
| 4,988,515 | 1/1991 | Buckberg | |
| 5,024,668 | 6/1991 | Peters et al. | 606/194 |
| 5,057,120 | 10/1991 | Farcot | 606/194 |
| 5,126,032 | 6/1993 | Manning | 514/718 |

OTHER PUBLICATIONS

Size Specifications for Cardiovascular Catheters.
"Anatomy & Physiology", Arthur Guyton, Saunders College Publishing, 1985. pp. 430-431.
Abu-Nema et al., "Intraaortic Balloon Tamponade During Hemorrhagic Shock in Sheep", *Circ. Shock* 24:55 (1988).
Emerman, C. L. et al., "Hemodynamic Effects of the Intra-Aotric Balloon Pump During Experimental Cardiac Arrest", *Am. J. Emerg. Med.* 7:378-383 (1989).
Manning, J. E. et al., "Selective Aortic Arch Perfusion: Description of a Technique With Potential Benefit in Cardiopulmonary and Cerebral Resuscitation", *Ann. Emerg. Med.* 19:212 (1990).
Spence, P. A. "Transfemoral Balloon Aortic Occlusion during Open Cardiopulmonary Resuscitation Improves Myocardial and Cerebral Blood Flow", *J. Surg. Research* 49:217-221 (1990).
Suzuki, A. et al., "Experimental Study on Cardiac Resuscitation", *Jpn. J. Anesthesiol.* 29:677 (1980) (Abstract).

*Primary Examiner*—John D. Yasko
*Assistant Examiner*—Corrine Moglione
*Attorney, Agent, or Firm*—Browdy and Neimark

[57] ABSTRACT

A method and apparatus for carrying out aortic occlusion along with oxygen carrying fluid infusion for use during CPR including the use of a specially constructed balloon catheter which, when inflated, occludes the aorta such that an óxygenated fluid infused through the catheter will be restricted to that part of the aorta above the balloon occlusion. The inner lumen of the catheter must have a diameter of at least two millimeters.

26 Claims, 4 Drawing Sheets

SELECTIVE AORTIC PERFUSION SYSTEM

FIELD OF THE INVENTION

The present invention relates generally to treatment of a patient during cardiopulmonary resuscitation (CPR) and more particularly to a process and apparatus for aortic occlusion along with oxygen carrying fluid infusion for use during CPR.

BACKGROUND OF THE INVENTION

Cardiopulmonary resuscitation has not fulfilled its original expectations, and the prognosis for patients remaining in cardiac arrest more than ten minutes remains poor (Becker AB, *Ann Emerg Med*, 20:355 (1991)). Indeed, cardiopulmonary resuscitation has recently been termed a "spectacular failure" in which only a small minority of patients have been successfully resuscitated (Barsan WG, *JAMA*, 265:3115-3118 (1991)). Standard advanced cardiac life support (ACLS) has only limited efficacy after the first few minutes of cardiac arrest. Studies in animal models have shown that vital organ blood flow, and thus oxygen delivery, during CPR is poor (Ditchey RV, et al, *Circ*, 66:297-302(1982); Ditchey RV et al, *Cardiovasc Res*, 19:419-425 (1985); and Taylor RB, et al, *Resuscitation*, 16:107-118(1988)). Indeed, CPR generally provides only a small fraction of normal oxygen supply to the brain and heart, and even less to other organs. Recent human studies have confirmed that perfusion pressures, the driving force for organ blood flow, are inadequate in humans during CPR (Paradis NA, et al, *Circ*, 80:361-368 (1989); Paradis NA, et al, *JAMA*, 263:1106-1113 (1990); and Martin GB, et al, *Ann Emerg Med*, 15:125-130(1986)). High-dose epinephrine, open chest CPR, and cardiopulmonary bypass increase perfusion pressure (Paradis NA, et al, *JAMA*, 265:1139-1144 (1991); Martin GB, et al, *Ann Emerg Med*, 16:628-636 (1987); and Howard MA, et al, *Ann Emerg Med*, 15:664-665 (1986)). However, these are not effective in all patients, or require significant resources not generally available.

In an effort to find simple but effective methods to improve perfusion during CPR, a number of mechanical intravascular based therapies have been investigated. Among these are arterial and venous volume infusion and aortic occlusion (Gentile NT, et al, *Crit Care Med*, (1990) (in press); Abu-Nema T et al, *Circ Shock*, 24:55-62 (1988); Suzuki A et al, *Jpn J Anesthesiol*, 29:677-682 (1980); Spence PA, et al, *J Surg Res*, 49:217-221 (1990)); and Manning JE et al, *Ann Emerg Med*, 19:212 (1990). These techniques, however, have failed to improve outcome. Aortic counterpulsation may improve perfusion (Emerman CL, et al, *Am J Emerg Med*, 7:378-383 (1989)), but has the disadvantage of requiring complex equipment which limits its use. Simple balloon occlusion, with or without volume infusion, does not appear to be effective.

It is known to provide oxygenated fluorocarbon emulsions to transport oxygen to oxygen deprived brain tissue (see U.S. Pat. No. 4,927,623 to Long, Jr.). It is also known to provide a blood cardioplegic solution as a resuscitative fluid for reperfusion of patients with myocardial infarction (see U.S. Pat. No. 4,988,515 to Buckberg). Balloon catheter devices and methods are known for directing blood toward the heart during spontaneous circulation (see, for example, U.S. Pat. Nos. 4,531,936 to Gordon; 4,804,358 to Karcher et al; 4,601,706 to Aillon; and 4,459,977 to Pizon et al).

SUMMARY OF THE INVENTION

It is a primary object of the present invention to provide a process and apparatus for carrying out aortic occlusion along with oxygen carrying fluid infusion to the heart and brain as a therapy for cardiac arrest.

It is a further object of the present invention to increase the period of time for possible successful resuscitation during cardiac arrest.

The above objects are accomplished through the use of a specially constructed balloon catheter which, when inflated, occludes the aorta such that fluids infused through the catheter will be restricted to that part of the aorta above the balloon occlusion. An oxygenated fluid (such as either oxygenated fluorocarbons or stroma-free polyhemoglobin) is used as the infused fluid either in a pre-oxygenated state or after an oxygenator has oxygenated the fluid.

Aortic occlusion with oxygen-carrying fluid infusion will significantly improve oxygen supply for short periods of time to the heart and brain. The infusion of oxygen-carrying fluid will be retrograde up the descending aorta toward the head resulting in preferential infusion of the coronary and carotid arteries. Attempts at defibrillation after this period of improved perfusion of the cardiac muscle will result in significantly higher rates of return of spontaneous circulation when compared to standard CPR.

Placement of a balloon catheter in the descending aorta through the femoral artery is not difficult (Bregman D, et al, *Am J Cardiol*, 46:261-264 (1980)) and it may be possible to accomplish this even in a prehospital setting.

The catheter which is used for the present invention is specially designed so as to have a large infusion port. Known balloon catheters have an infusion lumen which is relatively small, designed for the delivery of drugs or small amounts of fluid or for measurement of blood pressure. The catheter of the present invention must be designed to permit the flow of large amounts of perfusion fluid.

As the success of defibrillation in return to spontaneous circulation will be greatly improved after the selective aortic perfusion of the present invention, it is expected that the process and apparatus of the present invention will supplant CPR alone and will be used in all emergency departments and other critical care areas, and potentially in all advanced life support ambulances.

The present invention further comprehends a kit for use in performing the process of the present invention, which kit will include a catheter, a supply of stroma-free polyhemoglobin (or other oxygen-carrying perfusion fluid) and, optionally, an oxygenator to cause oxygenation of the fluid prior to perfusion through the catheter. The kit will preferably also include all of the other paraphernalia for carrying out the process of the present invention.

BRIEF DESCRIPTION OF THE DRAWINGS

The above and other objects will be shown in more detail in the following detailed description of the preferred embodiments when read in conjunction with the attached drawings, in which.

DETAILED DESCRIPTION OF THE PREFERRED EMBODIMENTS

Figure 1:
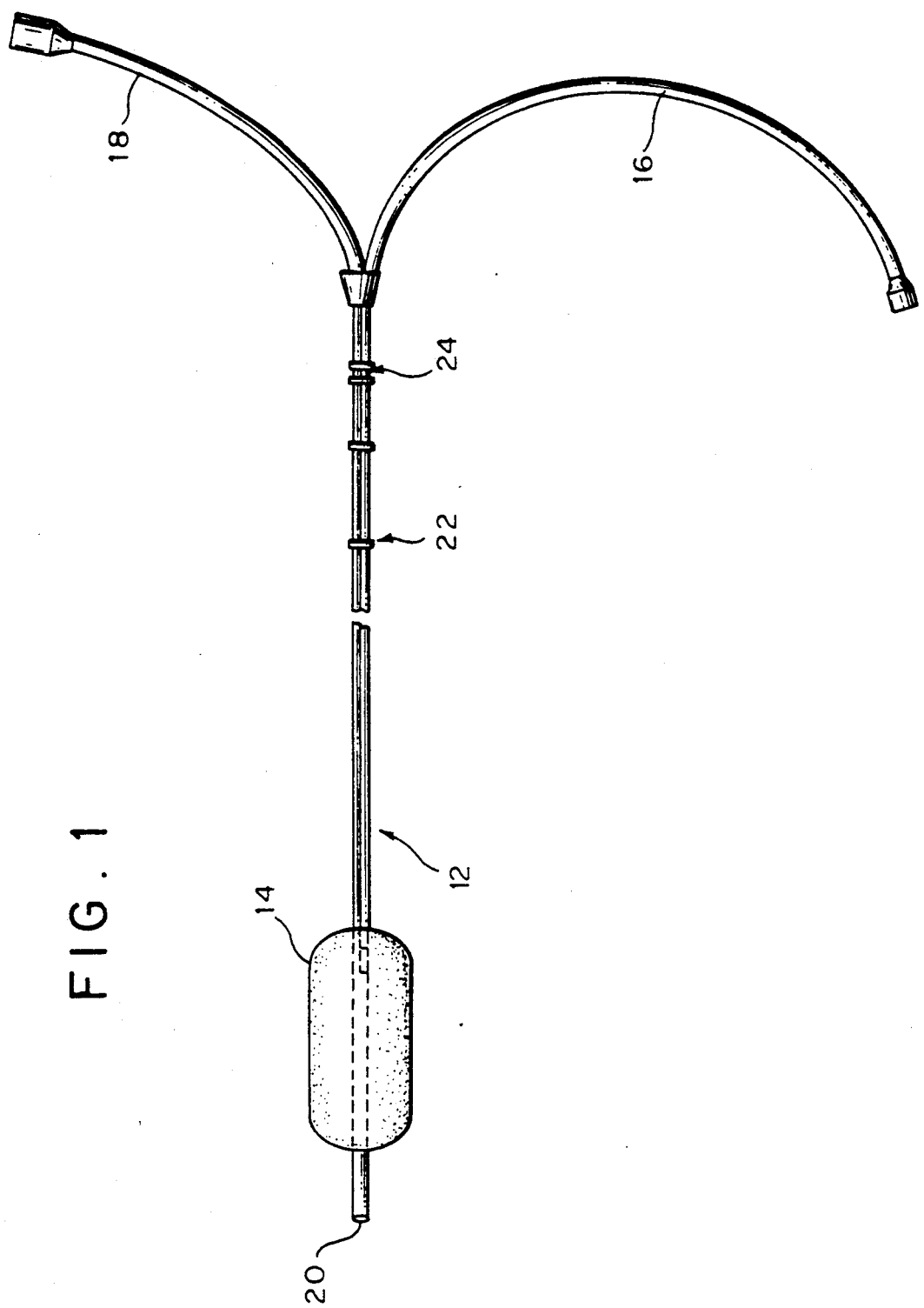
FIG. 1 is a schematic representative cross-section of a balloon catheter which can be used in accordance with the present invention.
Figure 5:
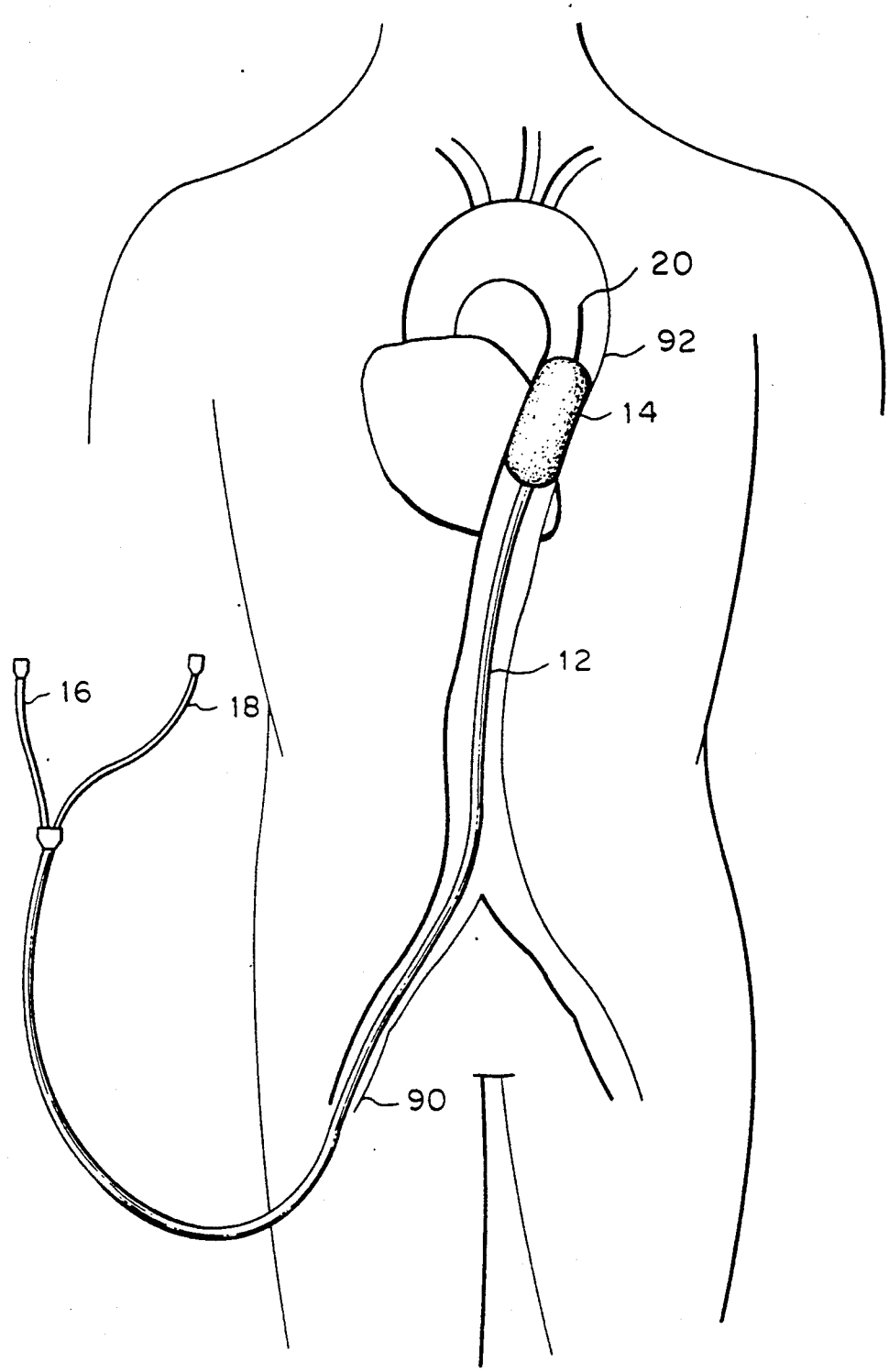
FIG. 5 is a diagrammatic representation showing the catheter in appropriate position during use.

The selective aortic perfusion system of the present invention has three major components. The first is a specially constructed balloon catheter 12 as shown in FIG. 1. This catheter is sized and dimensioned to permit insertion through the femoral artery and feeding up into the aorta until the balloon 14 is located in the descending aorta. Generally, the medical or paramedical personnel using this invention in an emergency setting will know when the balloon is in appropriate position when the tip of the catheter impacts the top of the aortic arch and cannot easily be maneuvered further through the aorta. Preferably, however, the catheter 12 will include markings 22, 24 which signal the distance from the marking to the tip 20 of the catheter 12. for example, a double mark 24 may mean that the distal tip is 70 cm away with each single mark 22 being in 2 cm increments. The person inserting the catheter 12 will know the position of the balloon 14 in the aorta from a consideration of the markings at the proximal end of the catheter. When the balloon 14 is in position and is inflated, it will occlude the aorta above the level of the diaphragm (see FIG. 5). Thus, infused fluids will be restricted only to the volume of the aorta and associated arteries above the balloon occlusion.

The catheter 12 is constructed to have two lumens 16, 18. The smaller lumen 16 is used for inflating the balloon. This lumen 16 can be attached to, for example, a 30 cc syringe (not shown) filled with saline. In the rare event of a balloon failure, only saline fluid would be released into the aorta. The larger lumen 18 opens distal to the balloon 18 at a point 20 and is attached to the system for infusion of oxygen containing fluid. The lumens 16, 18 may be side by side or coaxial.

The larger lumen 18 distinguishes the catheter of the present invention from all prior art balloon catheters. The cross-section of this lumen must be large enough to permit sufficient infusion of oxygenated fluid to oxygenate the myocardium and the cerebrum. It has been calculated that to completely replace all of the oxygen deficit which occurs after eight minutes of cardiac arrest, including the ongoing deficit thereafter, a total of four liters of fully oxygenated stroma-free polyhemoglobin would have to be infused over the course of two minutes. It should not be necessary, however, to infuse 100% of the oxygen deficit. Thus, it is fully expected that a replacement of 50% of the oxygen deficit, i.e., two liters of fluid over a course of two minutes, will provide results which are substantially better than standard CPR and yet avoid a possible volume overload when spontaneous circulation returns. Indeed, CPR is occasionally successful despite providing significantly less oxygen supply. Thus, 0.25-1.5 liters will most probably be sufficient in practice, up to a maximum of 3 liters (when fully oxygenated SFPH is used as the fluid) over the course of about one to three minutes.

The appropriate size lumen to permit this much infusion over the specified time period can be designed using standard engineering formulas, such as Poiseuille's Law, and/or empirical testing. The optimum diameter is on the order of about 2-3 mm so as to permit infusion without using excessive feed pressure while maintaining the catheter as a whole sufficiently small to permit insertion through the femoral artery. It is believed that the largest existing balloon catheters have an inner lumen of less than about 1 mm. For some applications, such as pediatric applications, the diameter may be as small as 1.5 mm and could be as large as 4 mm. Catheters of this large size can be easily placed using existing guide wire/introducer sheath techniques.

The most important function of the oxygenated fluid is to perfuse the myocardium, thereby permitting a vastly improved chance of return to spontaneous circulation after defibrillation. It is a secondary function to oxygenate the brain in order to prevent damage to the brain during the period of cardiac arrest. However, a prompt return to spontaneous circulation after perfusion of the myocardium and defibrillation will serve the purpose of oxygenating the cerebrum much better than the perfusion of oxygenated fluid in accordance with the present invention. In order to increase the amount of perfusion of the myocardium and cerebrum, it may be desirable to actually prevent flow of the perfusion fluid to the upper extremities by applying pressure to the appropriate arteries during infusion of the fluid. Furthermore, while it is permissible to continue CPR throughout the procedure of the present invention, it is permissible to suspend CPR once the catheter has been inserted, as the perfusion being caused by the infusion of oxygenated fluids will be much greater than that caused by the CPR. It may be desirable to leave the balloon fully or partially inflated after return of spontaneous circulation to continue preferential perfusion of the brain and heart.

The second component of the system of the present invention is oxygenated fluid. Currently, there are two types of artificial fluids which are used to carry oxygen for use in humans. The first is oxygenated fluorocarbons and the second is stroma-free polyhemoglobin. The amount of oxygen that can be carried by the fluorocarbons is limited because the total volume of fluorocarbons which can be dissolved in blood is limited. Stroma-free polyhemoglobin (SFPH) has a much greater oxygen carrying capacity (Sehgal LR et al, *Surgery*, 95:433-438 (1984)) and is thus preferred for this application. SFPH has recently been approved for preliminary human testing and is available from the Biopure Company.

Figure 2:
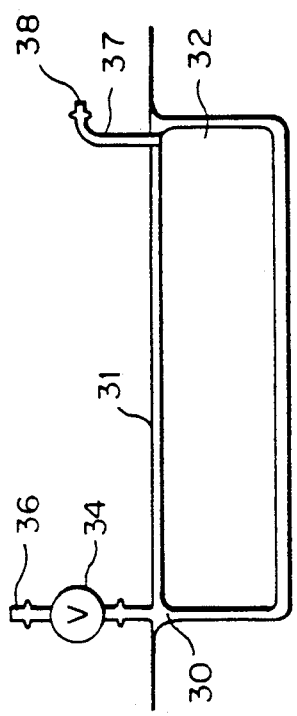
FIG. 2 is a schematic representative cross-section of a pressurizable container for use in dispensing oxygenatable fluid.

The stroma-free polyhemoglobin solution is preferably packaged in a special container capable of being pressurized, as shown in FIG. 2, so that it can be infused at pressures necessary to overcome those during the compression phase of CPR and necessary to provide a sufficient flow rate of oxygenating fluid. The stroma-free polyhemoglobin is stored in a pressure bag 32, preferably in a quantity of 500 cc or more. The bag is placed in a container 30 having a lid 31 sealed thereto. An inlet valve 34 in the lid 31 of the container includes a regulator mechanism (the details of which are well known and not shown) which permits entry of pressurized fluid at a specified maximum pressure regardless of the pressure of the fluid at the inlet of the valve 34. The valve 34 includes an inlet nozzle 36 which is connectable to the source of standardized pressurized oxygen available in all emergency and critical care settings. While pressurized oxygen is the preferred source of pressurized fluid to drive the feeding of the oxygenating fluid, it is to be understood that any other source of pressurized gas or liquid could be used for this purpose.

An outlet tube 37 connected to the interior of the bag 32 extends from the container 30 and includes a connector 38 for connection to the oxygenating fluid feeding lumen 18 of the catheter 12.

While the special container described above is the preferred means of dispensing the stroma-free polyhemoglobin solution, it should be understood that this particular means is not critical and that any manner of supplying the oxygenated fluid under pressure sufficient to provide the desired amount of infusion over the predetermined period of time can be used in the method of the present invention.

The oxygenating solution may also include the simultaneous infusion of other drugs or agents to improve myocardial and cerebral outcome. Any agent demonstrated to be effective when given intravenously may be more effective when administered to the heart and brain selectively by means of the present invention. Tissue salvaging agents in particular may be included in the oxygenated infusion fluid. Examples of agents which may be included in the oxygenated infusion fluid of the present invention are: epinephrine or other adrenergic agonists and pressors; antioxidants and free-radical scavengers such as the 21-amino steroids (lazaroids); anti-inflammatory agents including steroids and non-steroidal anti-inflammatory drugs such as a ibuprofen; calcium channel blockers such as lidoflazine, nimodipine, nicardipine, flunarizine, etc.; excitatory neurotransmitter blockers (NMDA receptor agonists) such as MK801, etc.; anticoagulants such as heparin; iron and heavy metal chelators such as deferoxamine; osmotic agents such as mannitol; anti-acidosis agents such as bicarbonate or dichloroacetate; insulin; antibodies such as anti-neutrophile antibody; and allopurinol. This list is intended to be exemplary only and not limiting.

Figure 3:
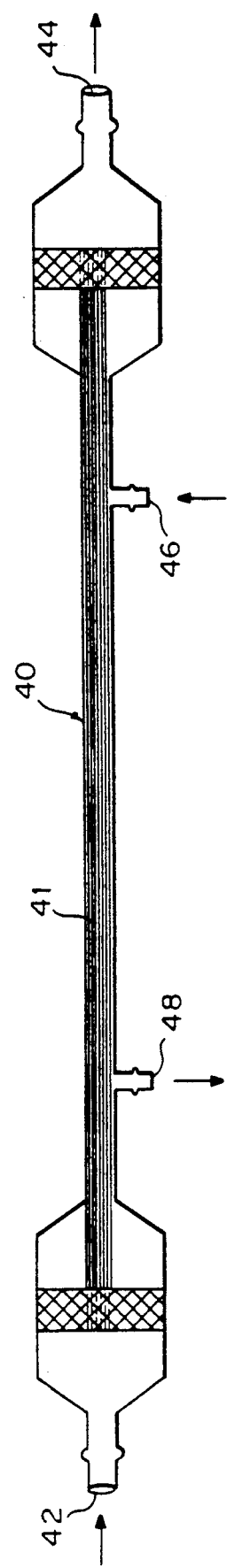
FIG. 3 is a schematic representative cross-section of an oxygenating system for use with the present invention.

The third component of the system of the present invention is an apparatus to oxygenate the stroma-free polyhemoglobin before infusion. This component is optional as the SFPH may be supplied already oxygenated and ready to use. However, as the SFPH may lose its oxygen over storage time it is preferred that the fluid be freshly oxygenated immediately prior to perfusion. Simple infusion of the solution into the arterial side of the circulation without pre-oxygenation would not improve the delivery of oxygen to the myocardium and brain. As shown in FIG. 3, a hollow fiber membrane oxygenator 40 having hollow fibers 41 can be placed in the system between the pressurized container 30 of stroma-free polyhemoglobin, at in-port 42 and the lumen 18 of the balloon catheter 12 at out-port 44. These systems allow the blood to flow around numerous hollow fibers 41 which have been specially constructed to allow diffusion of gas phase components without leakage of hemoglobin or blood. Oxygen is forced in at in-port 46 and exits at out-port 48. The mechanism of oxygenation is preferably countercurrent, which should result in oxygenation of the stroma-free polyhemoglobin, or other oxygenating fluid, to its maximum saturation. This device will also be constructed so that standard oxygen tanks or other emergency room oxygen supply can be used to supply it. The same oxygen can be used to inflate the pressure bag and drive the infusion as is used to oxygenate the fluid.

Figure 4:
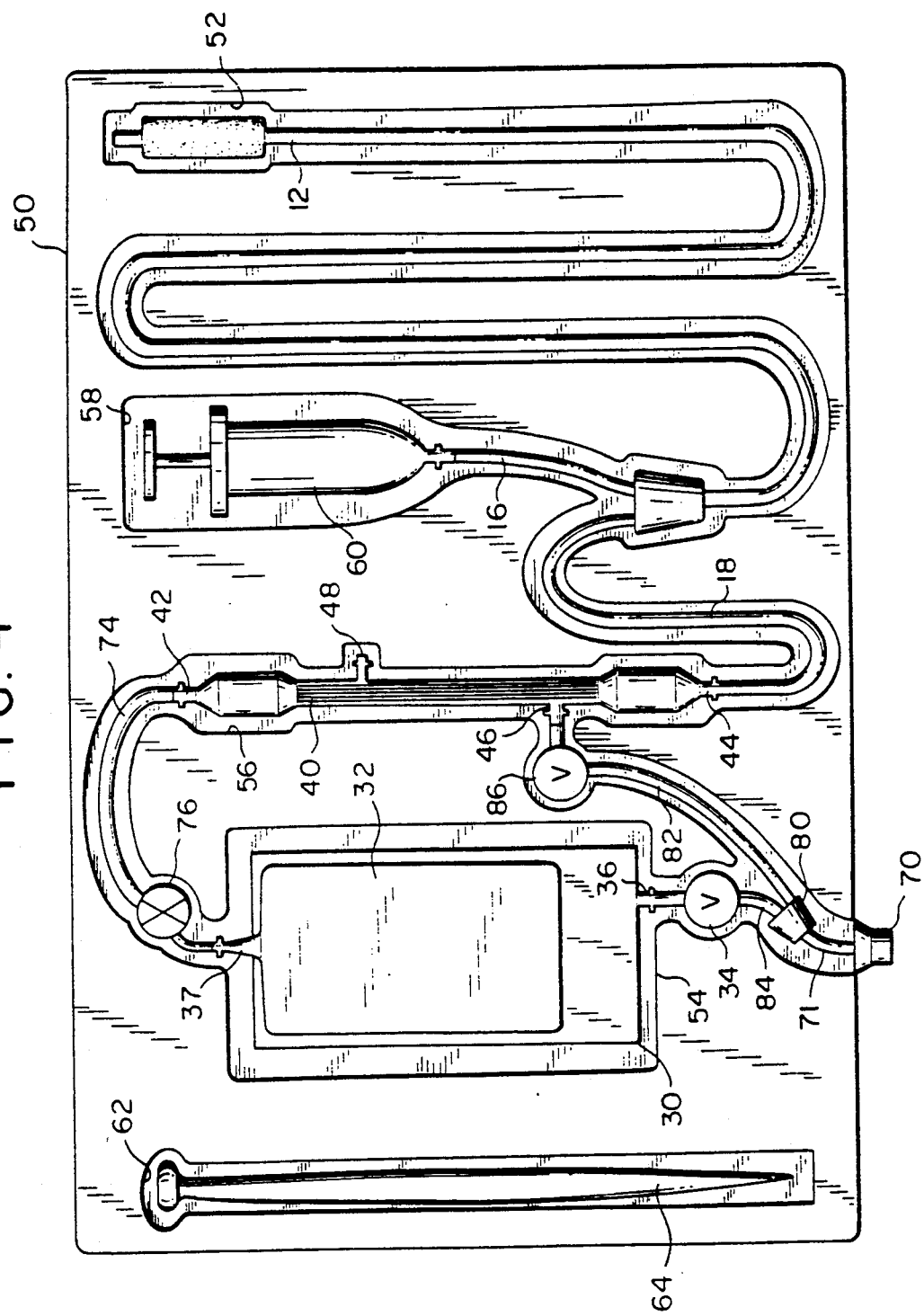
FIG. 4 is a diagrammatic representation of a kit in accordance with the present invention.

The components of the present invention are preferably packaged in kit form for use by medical and paramedical personnel. As shown in FIG. 4, the components may be packaged in a container 50, preferably a rigid plastic material molded to provide compartments for the various components of the kit. Compartment 52 holds the catheter 12, compartment 54 holds the container 30 with the sack 32 of stroma-free polyhemoglobin (or compartment 54 may comprise the container 30 and hold only the sack 32), and compartment 56 holds the oxygenator 40. Compartments for other paraphernalia necessary to implement the process of the present invention may also be present. For example, compartment 58 may be present for holding a syringe 60 to be used for inflation of the balloon and compartment 62 may be present to hold a catheter insertion sheath 64. Other components such as oxygenation tubing, guide wires, instructions for use, etc., may also be present.

The preferred kit form for use in the present invention is one which is the simplest and easiest to use in an emergency situation, which is often somewhat chaotic. Thus, the connections between the oxygenator and the source of stroma-free hemoglobin may be built-in so that the source of oxygenating fluid and the oxygenator need never be removed from the kit. Similarly, the connection between the oxygen output of the oxygenator and the pressure chamber of the oxygenating fluid compartment may be built into the kit, as may the connection between the balloon syringe and the catheter lumen leading to the balloon and the connection between the oxygenator fluid output and the catheter lumen for feeding the oxygenated fluid.

For example, as shown in FIG. 4, the oxygenator 40 may be sealed within the kit 50 with only an appropriate oxygen input nozzle 70 extending from the container. Nozzle 70, which extends from container 50 may be a standard connector for connection to a source of pressurized oxygen such as a standard oxygen tank or other emergency room oxygen supply. The nozzle 70 is connected within the container 50, by means of tube 71, to a Y-junction 80 which divides the oxygen input into line 82, which leads to the oxygen in-port 46 of the oxygenator, and line 84, which leads to the pressurizable container 30. The oxygen out-port 48 of the oxygenator may be vented to the atmosphere. All of these lines may be sealed within the container 50. The regulator valve 34 is also present within the container 50 so as to regulate the maximum pressure of fluid entering the container 30 for pressurizing the sack of oxygenating fluid 32. A rubber or plastic pressure bladder, not shown, may be placed between the sack 32 and the pressure chamber 30 to diminish risk of damage to sack 32. A second regulator valve 86 may also be built-in at the oxygen in-port 46 of the oxygenator 40 in order to regulate the pressure of oxygen entering the oxygenator 40.

The output port 37 from the sack 32 of oxygenating fluid may be directly connected to the oxygenating fluid inlet port 42 of the oxygenator 40 by means of a tube 74 sealed within the container 50. A valve 76, accessible from the outside of the container 50, may be used to open or close access of the oxygenating fluid from the sack 32 to the oxygenator input 42. The output from the oxygenator 40 through the out-port 44 may be directly connected to the fluid input cannula 18 of the catheter 12. Thus, no physical connections need be made by the emergency personnel except for attachment of an oxygen source to nozzle 70.

In use, the catheter 12 is removed from the compartment 52 of the kit. Lumen 18, which is much longer than is schematically shown in FIG. 4, is already connected to the output 44 of the oxygenator. Lumen 16 is also already connected to the syringe 60. Syringe 60 is preferably one which contains exactly the right amount of fluid to cause inflation of the balloon and is constructed so as to permit one-time use only. The use of such a pre-packaged syringe will eliminate the possibility of over-inflation and rupture of the balloon. A source of pressurized oxygen is connected to the nozzle 70 of the container 50.

The femoral artery 90 (see FIG. 5) will be punctured by a needle, through which a guide wire is advanced into the descending aorta 92. The guide wire may be any standard flexible guide wire or it could be a specially designed guide wire of increased stiffness to facilitate placement directly up the aorta. An introducer sheath 64 is removed from the compartment 62 of the container 50 and then advanced over the wire into the femoral artery. The central trochar and the guide wire are removed from the introduced sheath and the distal end 20 of the catheter 12 is introduced through the sheath into the femoral artery and fed until the balloon reaches the appropriate position in the aorta as determined by the markings 22 and 24 on the catheter or by other known means. Alternatively, the guide wire can be left in place to facilitate placement of the catheter 12, the guide wire being removed after placement of the catheter 12. The balloon 14 is then inflated by means of the syringe 60 and the valve 76 is opened in order to permit the feeding of the oxygenating fluid through the oxygenator 40 and into the lumen 18 and opening 20 into the aorta at the predetermined flow rate. At the same time, oxygen will flow through the oxygenator, countercurrent to the flow of oxygenating fluid, and into the pressure chamber 30 to drive the flow of oxygenating fluid at the predetermined rate, determined by the regulator valve 34. The oxygen output from the oxygenator may include a bleed valve to ensure flow of oxygen through the oxygenator even when not necessary for pressurization of the chamber 30.

This system will be efficacious in the treatment of cardiac arrest and its potential application is quite extensive. As stated previously, standard techniques for the treatment of cardiac arrest are useful only in the initial few minutes. It is believed that rapid application of the selective aortic perfusion system of the present invention will extend the period during which successful resuscitation could be obtained. The system should prove efficacious and it is believed that emergency departments and other critical care areas, and, potentially, life support ambulances, will be able to easily stock this particular piece of equipment and use the system of the present invention.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A method for improving and extending the period during which cardiopulmonary resuscitation can be successfully performed, comprising the steps of:
    placing a balloon catheter having an inflatable balloon through the femoral artery of a patient suffering from cardiac arrest, and feeding said catheter into the artery until the balloon is positioned in the descending aorta;
    inflating said balloon to occlude the aorta, whereby infused fluids will be restricted to the volume of the aorta above the balloon occlusion; and
    infusing an oxygenated fluid through a lumen in said balloon catheter to a point distal of said balloon.

2. The method of claim 1, wherein said balloon catheter is a double lumen catheter, a first lumen extending beyond the region of the balloon to carry fluid past the balloon occlusion when in use, and a second lumen being connected to the balloon to carry fluid for inflation of the balloon.

3. The method of claim 2, wherein said balloon is inflated with saline which is sent through said second lumen whereby, in the rare event of balloon failure, only saline will be released into the aorta.

4. The method of claim 1, wherein said oxygenated fluid is selected from the group consisting of oxygenated fluorocarbons and stroma-free polyhemoglobin.

5. The method of claim 1, further including the step of oxygenating the fluid prior to said infusing step.

6. The method of claim 5, wherein said oxygenating step is accomplished by passing the fluid through a hollow fiber membrane oxygenator.

7. An aortic perfusion catheter for use during cardiac arrest, comprising:
    a balloon catheter having first and second lumens and a balloon, said balloon catheter having a distal end, which is the end which first enters the body when in use, and a proximal end, which is the end opposite the distal end, and being sized and dimensioned to permit placement through the femoral artery with the balloon positioned in the descending aorta, said balloon being sized and dimensioned to occlude the descending aorta when in use;
    said first lumen passing through the catheter and opening into the aorta distal to the balloon when in use, and constituting means for infusing an oxygenated fluid into the aorta above said balloon; p1 said second lumen communicating from the proximal end of the catheter to the interior of the balloon for use in inflating the balloon,
    wherein said first lumen has an inner diameter of at least 1.5 mm.

8. A catheter in accordance with claim 7, wherein the inner diameter of said first lumen is about 3 mm.

9. An aortic perfusion catheter in accordance with claim 7, wherein said first lumen has a cross-section which is sufficiently large to permit infusion of at least 0.5 liters of fully oxygenated stroma-free polyhemoglobin in the course of two minutes.

10. An aortic perfusion catheter in accordance with claim 7, wherein said first lumen has a cross-section which is sufficiently large to permit infusion of at least 1.5 liters of fully oxygenated stroma-free polyhemoglobin in the course of two minutes.

11. An aortic perfusion catheter in accordance with claim 7, wherein said first lumen has a cross-section which is sufficiently large to permit infusion of at least 2.0 liters of fully oxygenated stroma-free polyhemoglobin in the course of two minutes.

12. An aortic perfusion catheter in accordance with claim 7, wherein said first lumen has a cross-section which is sufficiently large to permit infusion of at least 3.0 liters of fully oxygenated stroma-free polyhemoglobin in the course of two minutes.

13. An aortic perfusion catheter in accordance with claim 7, wherein said first lumen has a cross-section which is sufficiently large to permit infusion of at least 4.0 liters of fully oxygenated stroma-free polyhemoglobin in the course of two minutes.

14. A catheter in accordance with claim 7, wherein the inner diameter of said first lumen is at least about 3 mm.

15. A kit for use in aortic perfusion during cardiac arrest, comprising: p1 an aortic perfusion catheter in accordance with claim 7;
a container containing an oxygenatable fluid; and
packaging means for holding said catheter and said fluid container.

16. A kit in accordance with claim 15, further including oxygenator means for oxygenating said oxygenatable fluid.

17. A kit in accordance with claim 16, wherein said oxygenator means comprises a hollow fiber membrane oxygenator.

18. A kit in accordance with claim 15, wherein said packaging means has a separate catheter compartment for holding said catheter and container compartment for holding said container.

19. A kit in accordance with claim 18, wherein said packaging means further includes an external inlet means for connection to a source of pressurized fluid, said inlet means being in fluid communication with said container compartment, said container compartment being substantially pressure-tight to allow pressurization thereof upon supply of pressurized fluid thereto by means of said inlet means, thereby causing pressure to be applied to said oxygenatable fluid container.

20. A kit in accordance with claim 19, further including a regulator valve means, between said inlet means and said container compartment, for permitting only a maximum pressure of pressurized fluid to pass therethrough regardless of the pressure at said inlet means.

21. A kit in accordance with claim 19, wherein said packaging means includes external outlet means, in fluid communication with said oxygenatable fluid container, connectable to said first lumen of said catheter.

22. A kit in accordance with claim 21, further including oxygenator means for oxygenating said oxygenatable fluid and wherein said packaging means further includes a separate oxygenator compartment for holding said oxygenator means.

23. A kit in accordance with claim 22, wherein said oxygenator means includes an oxygen inlet, an oxygen outlet, an oxygenatable fluid inlet and an oxygenatable fluid outlet, said external inlet means being in direct fluid communication with said oxygen inlet of said oxygnator means.

24. A kit in accordance with claim 23, wherein said outlet external means is in direct fluid communication with said oxygenatable fluid outlet and said oxygenatable fluid inlet is in fluid communication with said oxygenatable fluid container.

25. A kit in accordance with claim 22, wherein said oxygenator means includes an oxygen inlet, an oxygen outlet, an oxygenatable fluid inlet and an oxygenatable fluid outlet, said outlet external means being in direct fluid communication with said oxygenatable fluid outlet and said oxygenatable fluid inlet being in fluid communication with said oxygenatable fluid container.

26. A kit in accordance with claim 15, further including a one-use syringe holding an amount of fluid calculated to fill the balloon of said catheter when injected through said second lumen without causing over-inflation thereof.

* * * * *